US00PP10898P

United States Patent [19]

van Rijn

[11] Patent Number: Plant 10,898

[45] Date of Patent: May 11, 1999

[54] CALATHEA PLANT NAMED 'CORA'

[75] Inventor: Magdalena J. M. van Rijn, Schipluiden, Netherlands

[73] Assignee: Rijnplant, Schipluiden, Netherlands

[21] Appl. No.: 09/006,833

[22] Filed: Jan. 14, 1998

[51] Int. Cl.[6] ..... A01H 5/00

[52] U.S. Cl. ..... Plt./375

[58] Field of Search ..... Plt./88.1, 375

[56] References Cited

U.S. PATENT DOCUMENTS

P.P. 9,692 11/1996 van Rijn ..... Plt./375

P.P. 9,693 11/1996 van Rijn ..... Plt./375

OTHER PUBLICATIONS

GTITM UPOV-ROM Citation for 'Cora' as per NL PBR 'MRA0013', Dec. 14, 1995.

*Primary Examiner*—Howard J. Locker
*Assistant Examiner*—Kent L. Bell
*Attorney, Agent, or Firm*—C. A. Whealy

[57] ABSTRACT

A distinct cultivar of Calathea plant named 'Cora', characterized by its upright and compact growth habit; moderate to rapid growth rate; dark green margin and stripes with light silvery green interveinal areas with reddish overtones on young leaves; and dark purplish red leaf petioles.

1 Drawing Sheet

BACKGROUND OF THE INVENTION

The present invention relates to a new and distinct cultivar of Calathea plant, botanically known as *Calathea roseo-picta*, and hereinafter referred to by the cultivar name 'Cora'.

The new Calathea was discovered by the inventor in a controlled environment in Schipluiden, The Netherlands, in March, 1989, as a naturally-occurring mutation of the non-patented *Calathea roseo-picta* cultivar 'Illustris'. The new Calathea was observed as a single plant with different leaf coloration in a group of plants of the parent cultivar. Leaves of plants of the parent cultivar 'Illustris' have dark green margins and stripes parallel to the primary veins with light green interveinal areas whereas leaves of plants of the new Calathea have dark green margins and stripes parallel to the primary veins with light silvery green interveinal areas with reddish overtones.

Asexual reproduction of the new Calathea by tissue culture or by division at Schipluiden, The Netherlands, has shown that the unique features of this new Calathea are stable and reproduced true to type in successive generations.

BRIEF SUMMARY OF THE INVENTION

The following traits have been repeatedly observed and are determined to be the unique characteristics of 'Cora'. These characteristics in combination distinguish 'Cora' as a new and distinct cultivar:

1. Upright and compact growth habit.
2. Moderate to rapid growth rate.
3. Dark green margin and stripes with light silvery green interveinal areas with reddish overtones on young leaves.
4. Dark purplish red leaf petioles.

The new Calathea has not been observed under all possible environmental conditions. The phenotype may vary somewhat with variations in environment such as temperature and light intensity, without, however, any variance in genotype.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top persepctive view of typical containerized plants of 'Cora'. The foliage colors in this photograph may appear different than the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe one-year old plants grown in 20-cm containers in Schipluiden, The Netherlands, in a glass-covered greenhouse with day and night temperatures of about 22° C. Light levels at plant level ranged from 2,000 to 3,000 lux.

Botanical classification: *Calathea roseo-picta* cultivar 'Cora'.

Parentage: Naturally-occuring mutation of *Calathea roseo-picta* cultivar 'Illustris' (not patented).

Propagation:

*Type.*—By tissue culture or by division.

*Time to rooting.*—Summer: About 12 weeks with temperatures of about 22° C. Winter: About 16 weeks with temperatures of about 22° C.

*Rooting habit.*—Fibrous, thin, strong.

Plant description:

*Appearance.*—Upright and compact; tender evergreen herbaceous plant. Appropriate for 9 to 40-cm containers.

*Plant height from soil level to top of plant plane.*—About 75 cm.

*Plant width.*—About 62.5 cm.

*Branching habit.*—Freely branching.

*Growth rate.*—Moderate to rapid.

*Vigor.*—Moderate.

*Crop time.*—From a tissue-cultured plantlet, about 8 to 10 months are required to produce a finished plant in a 17-cm container about 65 cm high.

*Foliage description.*—Single, symmetrical. Length: About 35 cm. Width: About 23 cm. Shape: Ovate. Apex: Mucronate. Base: Rounded, obtuse. Margin: Entire. Texture: Leathery, glabrous. Surface: Midrib sunken on upper, protruding on lower surface. Leaf blade slightly concave between veins. Petiole: Length: About 40 cm. Wings: Length: About 9 cm. Width: About 8 mm. Geniculum: Length: About 3.5 cm. Width: About 5 cm. Color: Dark green margins and stripes parallel to the primary veins with light silvery green interveinal areas with reddish overtones. Young leaves, upper surface: Thin outer margin, about 1 mm in width, 60A. Inside margin, about 3.5 cm in width, 144A. Dark green stripes, about 1.5 to 2 cm in width, 137A. Interveinal areas, about 2 to 3 cm in width, 139D. Reddish overtones, close to 63C. Young leaves, under surface: 187A, dull. Mature leaves, upper surface: Thin outer margin, about 1 mm in width, 60A. Inside margin, about 3.5 cm in width, 139A. Dark green stripes, about 1.5 to 2 cm in width, 139A. Interveinal areas, about 2 to 3 cm in width, 139D. Mature leaves, under surface: 187A, dull. Venation, upper surface: Midrib at base greenish with reddish flush, becoming brighter in color towards the apex; primary veins, dark green, 139A. Venation, under surface: Midrib 183A, dull. Petiole: 187A. Petiole wings: 187C. Geniculum: 178A.

Flower description: Flowers have not been observed on any plants of the new Calathea.

Disease resistance: Resistance to known Calathea diseases has not been observed to date on plants grown under commercial greenhouse conditions.

It is claimed:

1. A new and distinct cultivar of Calathea plant named 'Cora', as illustrated and described.

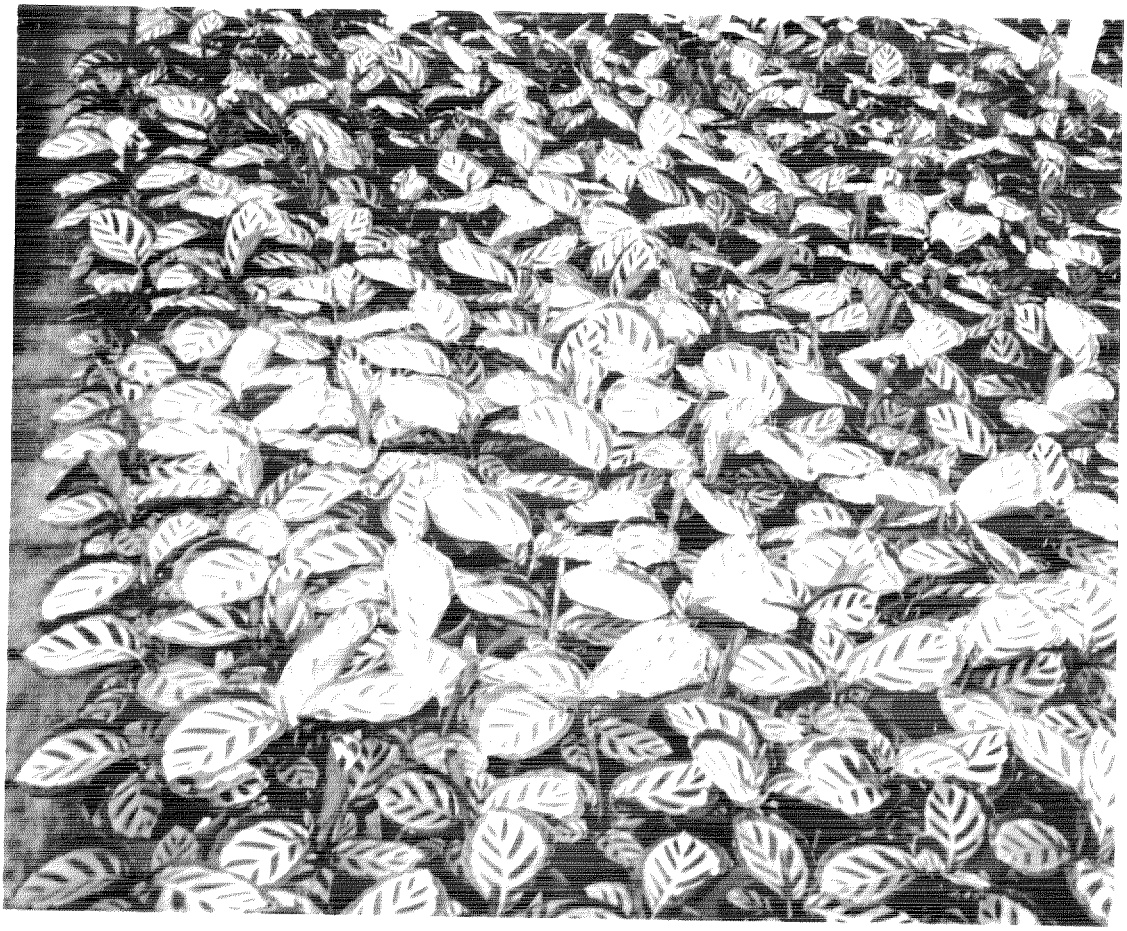

* * * * *